US012658294B2

(12) United States Patent
Robert Martin

(10) Patent No.: US 12,658,294 B2
(45) Date of Patent: Jun. 16, 2026

(54) HEALTHCARE MEMBERSHIP CARD AND METHOD OF USE

(71) Applicant: James Robert Martin, St. George, UT (US)

(72) Inventor: James Robert Martin, St. George, UT (US)

( * ) Notice: Subject to any disclaimer, the term of this patent is extended or adjusted under 35 U.S.C. 154(b) by 0 days.

(21) Appl. No.: 18/986,071

(22) Filed: Dec. 18, 2024

(65) Prior Publication Data

US 2025/0218558 A1    Jul. 3, 2025

Related U.S. Application Data

(60) Provisional application No. 63/616,305, filed on Dec. 29, 2023.

(51) Int. Cl.
*G16H 10/65* (2018.01)
*G06Q 20/34* (2012.01)

(52) U.S. Cl.
CPC ........... *G16H 10/65* (2018.01); *G06Q 20/341* (2013.01); *G06Q 20/3572* (2013.01)

(58) Field of Classification Search
CPC ... G16H 10/65; G06Q 20/341; G06Q 20/3572
See application file for complete search history.

(56) References Cited

U.S. PATENT DOCUMENTS

| | | | | |
|---|---|---|---|---|
| 6,121,544 A * | 9/2000 | Petsinger | ............. | G06K 19/005 |
| | | | | 150/147 |
| 2013/0334306 A1* | 12/2013 | Kaperst | ............. | G06Q 20/3574 |
| | | | | 235/492 |
| 2016/0217455 A1* | 7/2016 | Hosny | ................ | G06Q 20/4012 |
| 2017/0017871 A1* | 1/2017 | Finn | ......................... | H01Q 7/00 |
| 2021/0279719 A1* | 9/2021 | Kamaal | ............. | G06Q 20/3572 |

OTHER PUBLICATIONS

Smart Card Technology in U.S. Healthcare: Frequently Asked Questions, A Smart Card Alliance Healthcare Council Publication, Sep. 2012.*

* cited by examiner

*Primary Examiner* — Joshua B Blanchette
(74) *Attorney, Agent, or Firm* — Gurr & Brande, PLLC; Robert A. Gurr

(57) ABSTRACT
A healthcare membership card has a front surface and a rear surface. The front surface may have a first chip, card number, and other personal information (e.g., name and address). The rear surface may have a second chip, a first magnetic strip, a second magnetic strip, a QR code, and/or one or more phone numbers. The first chip and first magnetic strip may process payments from a health saving account or health reassignment account, thereby allowing a user to make payments for medical expenses directly to the healthcare provider. The second chip and second magnetic strip may facilitate payment from a health sharing account (or other account).

8 Claims, 6 Drawing Sheets

300

312

402

404

HEALTHCARE MEMBERSHIP CARD AND METHOD OF USE

CROSS-REFERENCE TO RELATED APPLICATIONS

This application claims the benefit of U.S. Provisional Application Ser. No. 63/616,305, filed on Dec. 29, 2023, which is incorporated herein by reference.

TECHNICAL FIELD

The present disclosure relates to a healthcare membership card. More particularly, the present disclosure relates to a healthcare membership card that allows access to medical records and more than one health/payable account.

BACKGROUND

There have been many forms of non-traditional health insurance used in recent years, such as health savings accounts and health share entities. Health savings accounts have helped many individuals with high-deductible health plans. These types of accounts allow individuals to deposit tax-free money that may be accessed when health care expenses need to be paid. The individual over the account controls the account instead of an employer or insurance company. Health share entities create plans where members may share medical expenses. Such plans typically require an individual to pay a certain share each month and an annual share.

Currently, an individual is required to carry a card or check for a health savings account or health reassignment account. However, there is no immediate payment source for a health share. Because of this, health share entities, such as Christian Healthcare Ministries, Sedera, Liberty, and others, function with a reimbursement model. These models usually result in months of processing time with many people and entities involved, which increases costs and frustration. In particular, three months to a year or longer is not uncommon for current processing times for reimbursement. For many, this delay creates a financial difficulty.

Historically, the trigger for the payment of a medical need begins after the need has been handled, thereby removing any negotiation or leverage. This leverage is also lost due to a third party handling the money flow after the medical need has been addressed. The third party (usually an insurance entity or other 'for profit entity' such as pharmacy benefit management in the pharmaceutical space), is positioned to intercept the flow of payment and information. Consequently, the patient lacks understanding of who is getting paid and how much, even though the patient must pay. Unfortunately, the providers and other medical entities set prices according to what a third party is willing to pay, rather than a fair rate to the patient.

Accordingly, there is a need for a healthcare membership card that allows an individual to directly pay money before, during, or after a medical procedure to a healthcare provider from a health savings account and/or a health share account. The present disclosure seeks to solve these and other problems.

SUMMARY OF EXAMPLE EMBODIMENTS

In one embodiment, a healthcare membership card comprises a front surface and a rear surface. The front surface may comprise a chip, card number, and other personal information (e.g., name and address). The rear surface may comprise a first magnetic strip, a second magnetic strip, a QR code, and one or more phone numbers. The first magnetic strip may process payments from a health savings account or health reassignment account, thereby allowing a user to make payments for medical expenses directly to the healthcare provider. The second magnetic strip may facilitate payment from a health sharing account. In some embodiments, the healthcare membership card further comprises an inner layer between the front surface and the rear surface having a faraday shield or RFID-blocking material to prevent misreading payment modalities such as a chip or a wireless tap account on the rear surface when the user intends to pay with a separate chip or wireless tap account on the front surface and vice versa.

The rear surface may also comprise a QR code which may be scanned to access a link to a patient's individual medical health record. The health record may include personal information, such as name, age, address, last visit to a provider, health share plan, family history, or any other type of personal information. Furthermore, the one or more numbers may include a medical line that allows access to a 24/7 advanced practice clinician (e.g., Physician Assistant or Nurse Practitioner). Other numbers may include a member advocate number with live 24/7 availability to assist a user in the processing of medical or healthcare bills.

DETAILED DESCRIPTION OF EXAMPLE EMBODIMENTS

Figure 1:
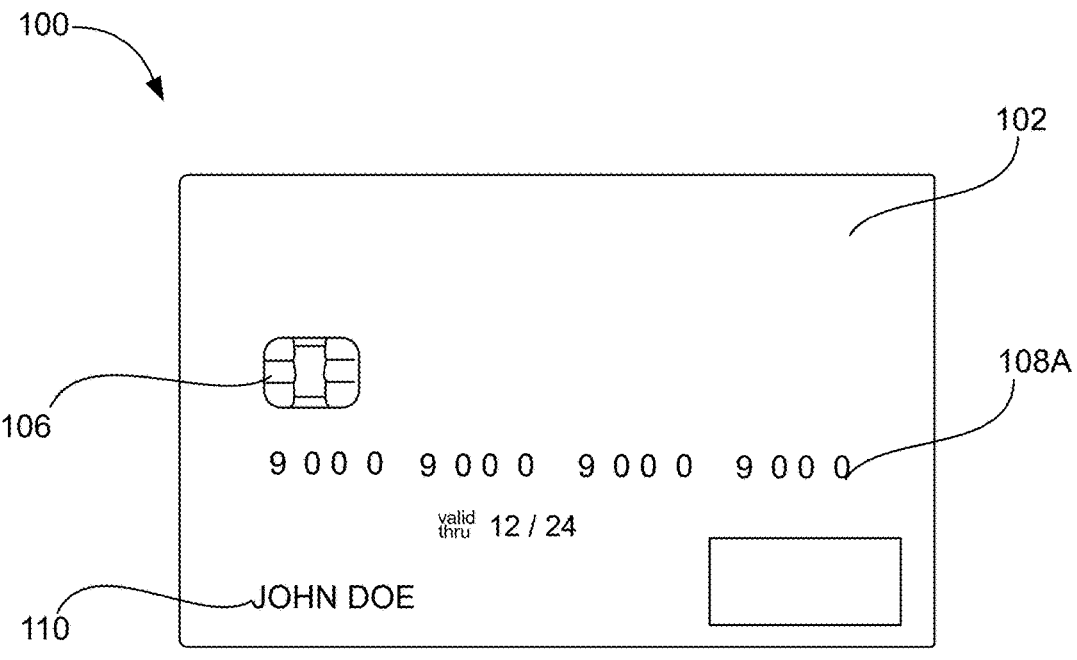
FIG. 1 illustrates a front elevation view of a healthcare membership card.

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may.

Accordingly, the particular arrangements disclosed are meant to be illustrative only and not limiting as to the scope of the invention, which is to be given the full breadth of the appended claims and any and all equivalents thereof. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various sequences and arrangements while still falling within the scope of the present invention.

The term "coupled" may mean that two or more elements are in direct physical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including, but not limited to," the term "having" should be interpreted as "having at least," the term "includes" should be interpreted as "includes, but is not limited to," etc.).

As previously discussed, there is a need for a healthcare membership card that allows an individual to directly pay money before, during, or after a medical procedure to a healthcare provider from a health savings account and/or a health share. There is also a need to provide easy access to individual/health information. This reduces the time required to pay bills and also allows the patient to be informed as to the cost of the procedure, among other things. The healthcare membership card disclosed herein seeks to solve these and other problems.

The healthcare membership card disclosed herein generally comprises a front surface and a rear surface. The front surface may comprise a chip, card number, and other personal information (e.g., name and address). The rear surface may comprise a first magnetic strip, a second magnetic strip, a QR code, and one or more phone numbers. It will be appreciated that the membership card allows a user (e.g., patient) to make payments from both a health savings account or health share from the same card. It should be noted that making payments from the health share directly to the healthcare provider removes the need of having a third party, thereby decreasing costs and waiting times for received medical procedures.

Figure 2:
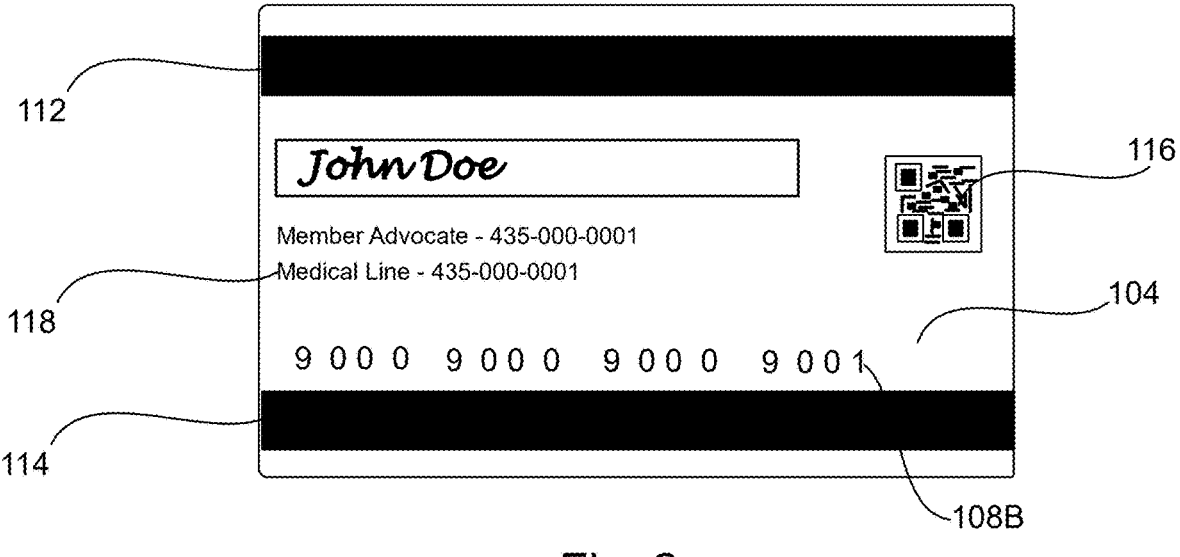
FIG. 2 illustrates a rear elevation view of a healthcare membership card.

Referring now to FIGS. 1-2, in some embodiments, the healthcare membership card 100 comprises a front surface 102 and a rear surface 104. The front surface 102 may comprise a chip 106 corresponding to a first card number 108A of a first account, and other personal information 110 (e.g., name and address). The rear surface 104 may comprise a first magnetic strip 112 corresponding to the first card number 108A, a second magnetic strip 114 corresponding to a second card number 108B of a second account, a QR code 116 (or other machine-readable code), and one or more phone numbers 118. The first magnetic strip 112 may process payments from a health saving account or health reassignment account, thereby allowing a user to make payments for medical expenses directly to the healthcare provider. The second magnetic strip 114 may facilitate payment from a health sharing account. Accordingly, depending on the type of procedure and/or the cost, the user may use either the first magnetic strip 112, the second magnetic strip 114, or both. While the first and second magnetic strips 112, 114 may be connected to the health savings account or health share account, respectively, it will be appreciated that any other account may be connected with the first or second magnetic strips 112, 114, such as a personal savings or checking account.

The rear surface 104 may also comprise a QR code 116 which may be scanned to access a patient's individual medical health record. The health record may include personal information, such as name, age, address, last visit to a provider, health share plan, family history, or any other type of personal information. Not only is this information helpful for a healthcare provider, but it is also useful for a user. For example, if a user wants to know the status of their bills or their health, the user may scan the QR code 116 to access the personal information. In some embodiments, a provider may also scan the QR code 116 to access the information. In one embodiment, access to the information may be password/passcode restricted to guard against unauthorized access. For example, after scanning the QR code 116, the user's last four digits of their social security number (or other code) may be required before the information is displayed.

Furthermore, the one or more numbers 118 may include, in some embodiments, a medical line that allows access to a 24/7 advanced practice clinician (e.g., Physician Assistant or Nurse Practitioner). The advanced practice clinician can direct the medical care. Other numbers may include a member advocate number with live 24/7 assistance to aid a user in the processing of medical or healthcare bills. The member advocate is available to forward or charge the card with the appropriate amount of money to pay the medical bill. It will be appreciated that the membership card 100 allows a user to access all accounts and personal information from a single, easy to use card, overcoming limitations in the art.

It will further be appreciated that the membership card 100 may assist in the following areas: (1) overinflated rates are decreased by having real-time negotiation and immediate electronic cash payment prior to, during, or immediately following the time of the medical procedure or service; (2) long payment processing times are decreased by being able to immediately make payments; (3) the amount of labor involved in a transaction is decreased by removing an unnecessary third party, thereby decreasing costs for both the user and healthcare provider; (4) the user's personal medical information is available through the QR code, which may lead the user to their personal medical record; and (5) the user may have 24/7 access (or other access) via the one or more phone numbers described above.

Additionally, the healthcare membership card 100 solves the problem of a third party controlling the costs and services in the medical industry. Currently, the user/patient is blind to the medical cost. The third party (usually an insurance entity) is positioned to intercept the flow of payment and information. Then, the third party delivers the information to a provider. Consequently, the user lacks control over who is being paid and the amount they are being paid. Often, prices for medical procedures are set by the amount third parties are willing to pay healthcare providers and other medical entities, which may make a rate a lot higher than it should be. The healthcare membership card 100 eliminates the third-party payment system and restores a two-party payment system. In particular, a member is in direct communication with the provider, allowing the member to use the membership card 100 to directly pay and communicate with the provider.

In some embodiments, the healthcare membership card may be integrated into a mobile application. For example, a user may access all their information, medical phone numbers, and payment options on the mobile application. A user may then use NFC, Bluetooth®, or other wireless methods to make payments, eliminating the third-party control and delay.

Figure 3:
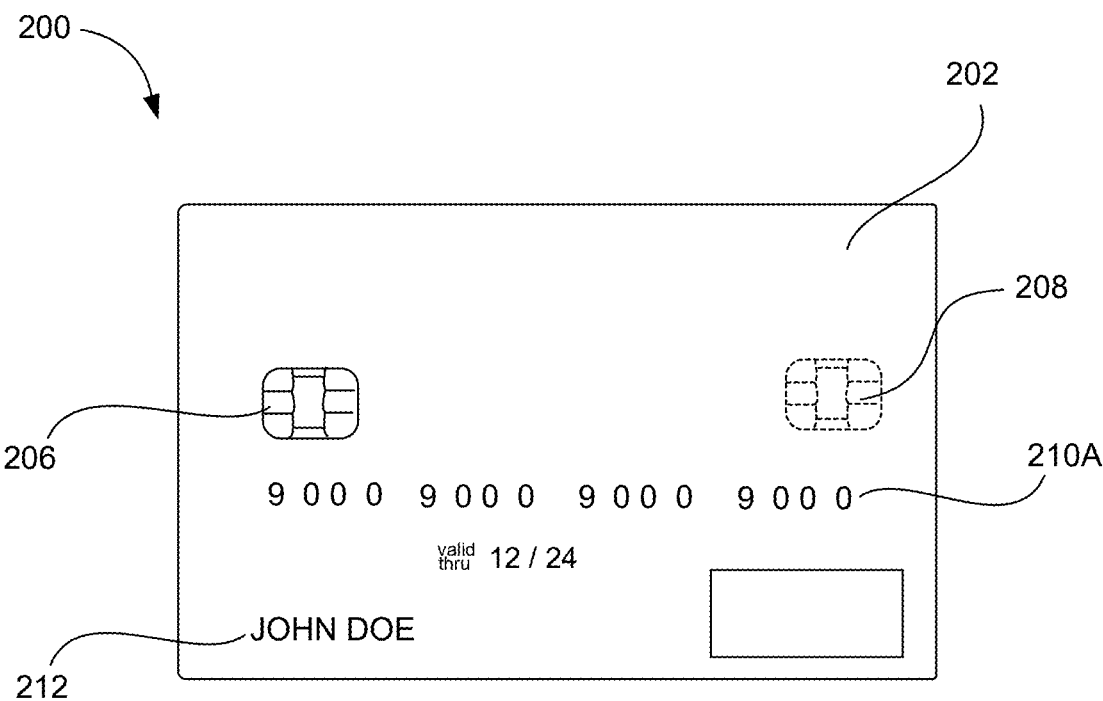
FIG. 3 illustrates a front elevation view of a healthcare membership card.
Figure 4:
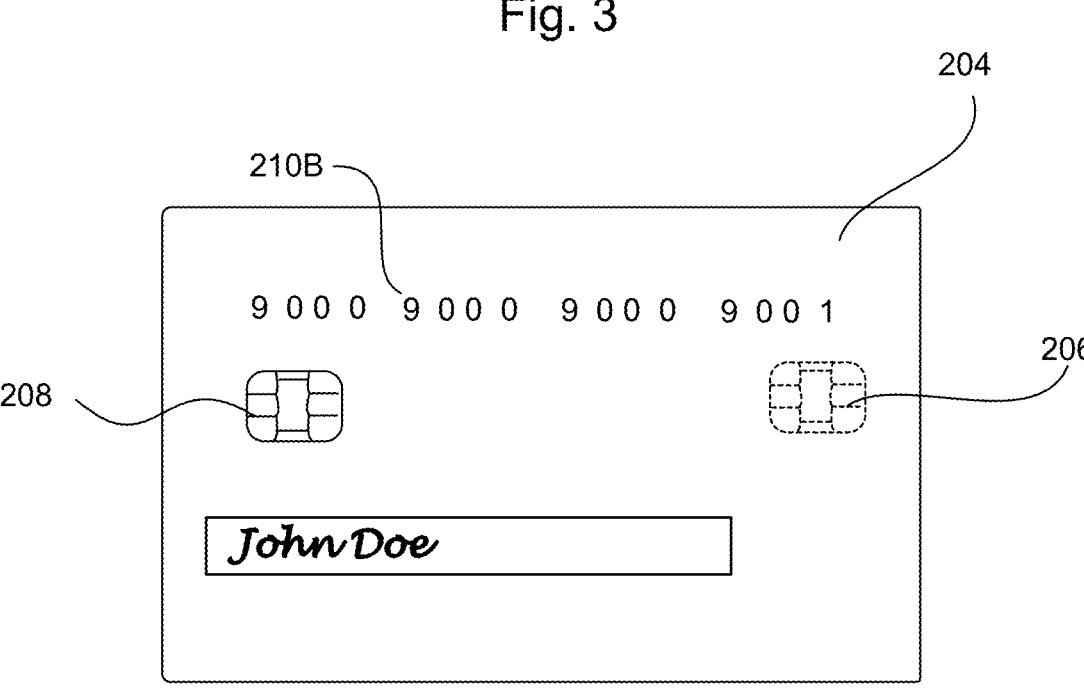
FIG. 4 illustrates a rear elevation view of a healthcare membership card.

In some embodiments, as shown in FIGS. 3-4, a healthcare membership card 200 comprises a front surface 202 and a rear surface 204. The membership card 200 may comprise a first chip 206, a second chip 208, at least one card number 210A-B corresponding to the chips 206, 208, respectively, and other personal information 212 (e.g., name, address, etc.). The first chip 206 may allow access to a first account while the second chip 208 may provide access to a second account. As shown, in some embodiments, the first chip 206 is positioned on the front surface 202 while the second chip 208 is positioned on a rear surface 204 opposite the front surface 202.

Figure 5:
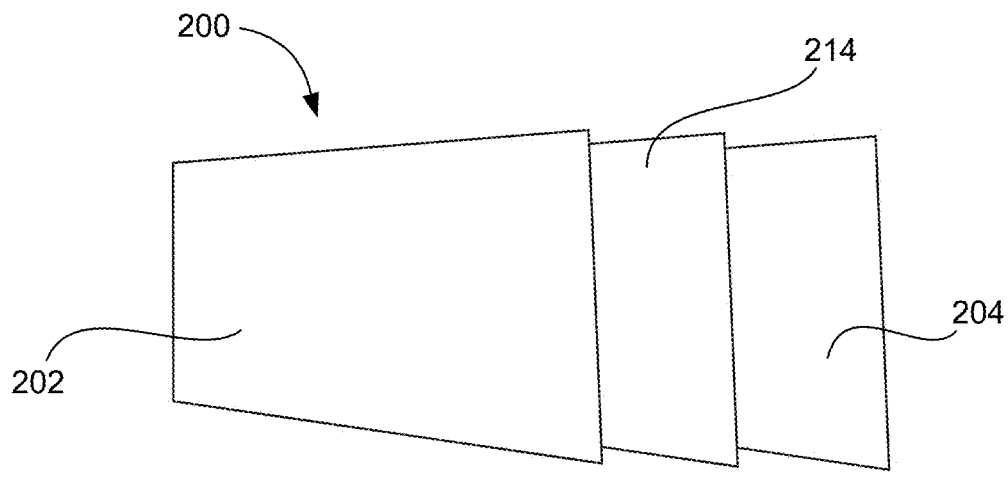
FIG. 5 illustrates a front perspective, exploded view of a healthcare membership card.

Referring to FIG. 5, an exploded view of a healthcare membership card 200 is shown comprising a first surface 202, a second surface 204, and an inner layer 214 interposed between the front surface 202 and the rear surface 204. The inner layer 214 comprises a faraday shield or RFID-blocking material that disrupts electromagnetic fields, such as carbon fiber or aluminum, configured to prevent a chip reader and/or RFID reader device from inadvertently scanning the incorrect chip. For example, referring to FIGS. 3-4 again, the inner layer 214 prevents scanning of the second chip 208 when the first surface 202 is placed on the chip reader, and likewise prevents the chip reader from scanning the first chip 206 when the second surface 204 is placed on the chip reader.

It will be appreciated that the card 200 may allow a user to access multiple accounts on a single membership card. For example, when a user needs to pay for a medical bill, the user has the option of using one or both health accounts on the card 200. The first and second chips 206, 208 may be connected to a health savings account or a health share account, respectively. However, it will be appreciated that any other account may be connected with the first and second chips 206, 208, such as a personal savings or checking account. Furthermore, other healthcare accounts may be used, such as individual accounts (HSA, HMA, HRA), community cash (charitable organizations), cooperative cash resources (healthshare organizations), friends and families accounts, and corporate/small business accounts. While first and second chips 206, 208 are illustrated, it will be appreciated that multiple magnetic strips may also be used for numerous accounts.

Figure 6:
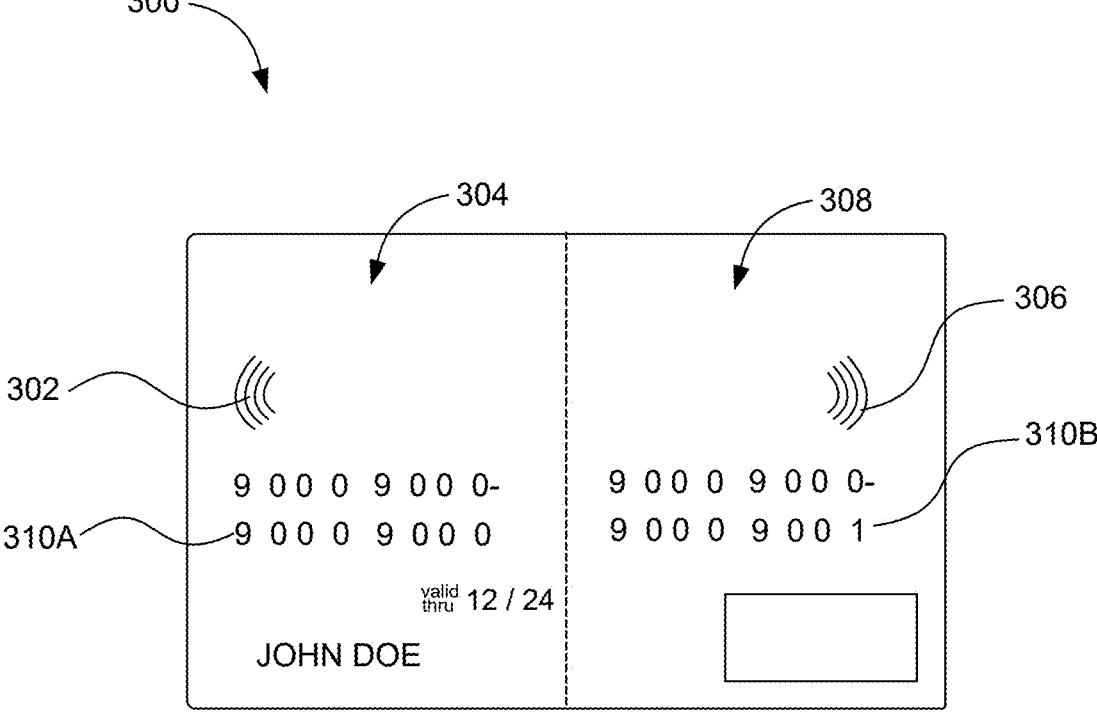
FIG. 6 illustrates a front elevation view of a healthcare membership card.

Referring to FIG. 6, in some embodiments, a membership card 300 may comprise a first wireless chip 302 on a first half 304 of the membership card 300 and a second wireless chip 306 on a second half 308. The wireless chips 302, 306 may be any known wireless or tap-capable chip in the art, such as NFC chips. Each wireless chip 302, 306 may be directed toward a distinct account, with corresponding account numbers 310A-B, allowing a wireless transaction instead of insertable chips or magnetic strips. While shown as being on separate halves 304, 308 of one side of the membership card 300, it will be appreciated that the wireless chips 302, 306 may be on opposite sides (e.g., front and back) of the membership card as well, as discussed with previous embodiments. In such embodiments, an inner, faraday layer 214 may also be used to prevent inadvertent wireless chip scanning.

Figure 7:
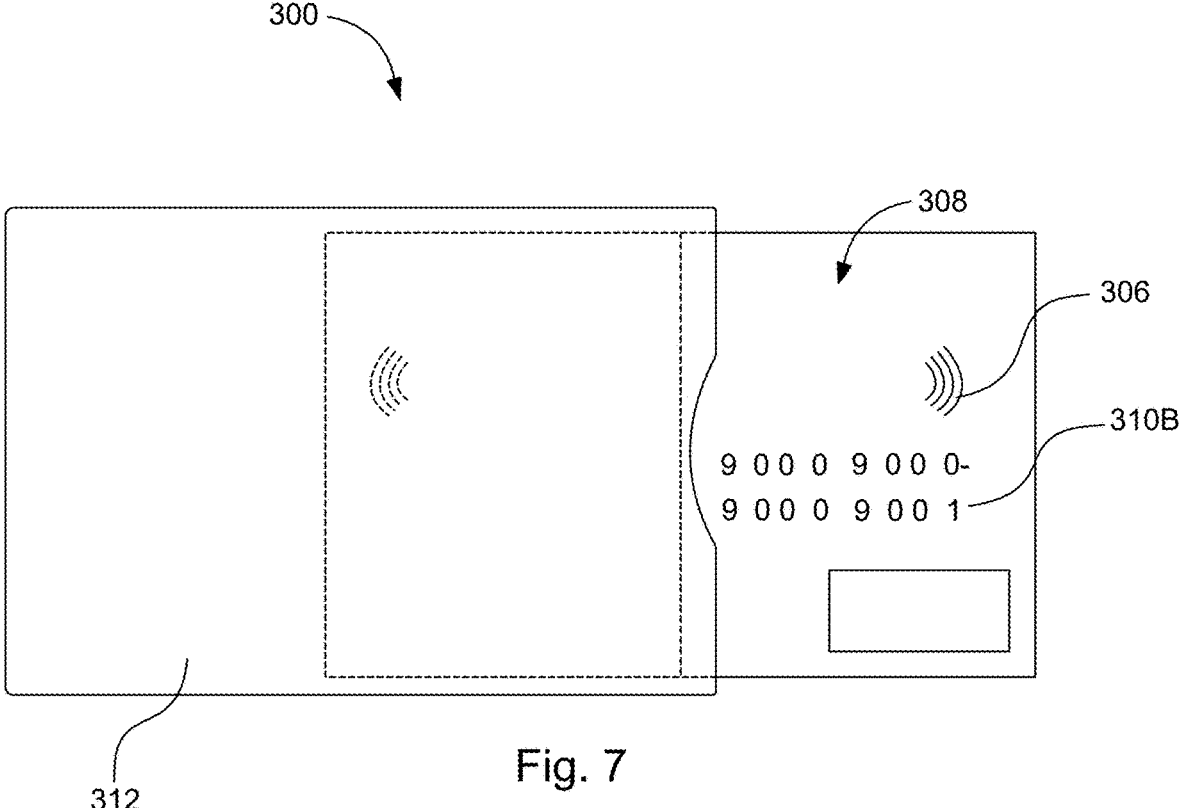
FIG. 7 illustrates a front elevation view of a healthcare membership card with faraday slip cover.

Referring to FIG. 7, in some embodiments, the membership card 300 comprises a faraday slip cover 312 for blocking signals to/from the unselected account. For example, if a user desires to utilize the second chip 306 with the second account 310B, a user may withdraw the membership card 300 from within the slip cover 312 so as to expose only the second half 308 of the membership card 300, ensuring that the first chip 302 remains within the faraday slip cover 312, thereby preventing a chip reader from inadvertently reading the incorrect chip and associated account. A user may freely remove and insert the membership card 300 into the faraday slip cover 312 so as to select the desired account for use.

It will be appreciated that each side of half of a membership card disclosed herein may comprise unique information and/or a unique appearance or ornamentation so as to allow a user to more easily identify the account to use. For example, one side (or half) may be a first color (e.g., blue) representing a first account, while the opposite side (or half) is a second color (e.g., red) representing a second account. If chips or magnetic stripes are on the same side, such as shown in FIGS. 2 and 6, each respective half of the card may be uniquely colored or otherwise customized.

In some embodiments, a membership card may comprise any combination of chips, magnetic strips, or tap (i.e., wireless) accounts with multiple payment modalities distributed on the front surface and/or the rear surface, which, in some embodiments, are separated by the inner layer 214. For example, in some embodiments, a membership card may comprise a chip reader and a wireless tap account. It will be appreciated that the inner layer 214 blocks any chips or wireless tap accounts on the opposite surface from being mistakenly scanned by a chip reader or RFID reader device when the user intends to pay with a chip or wireless tap account on the opposite surface, and vice versa.

Figure 8:
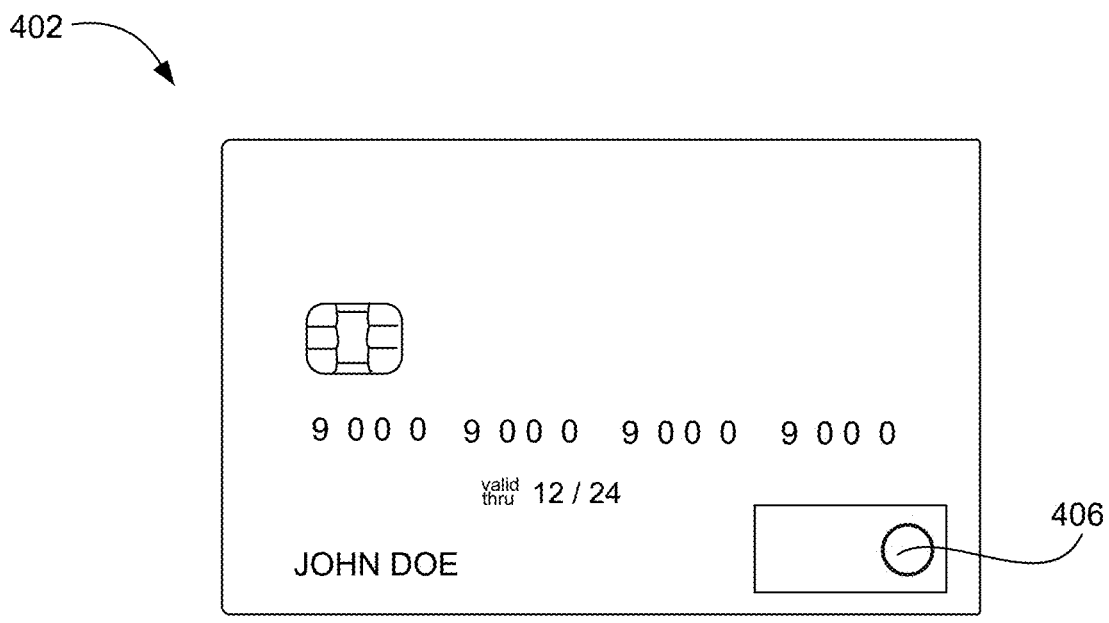
FIG. 8 illustrates a front elevation view of a first membership card of a membership card assembly.
Figure 9:
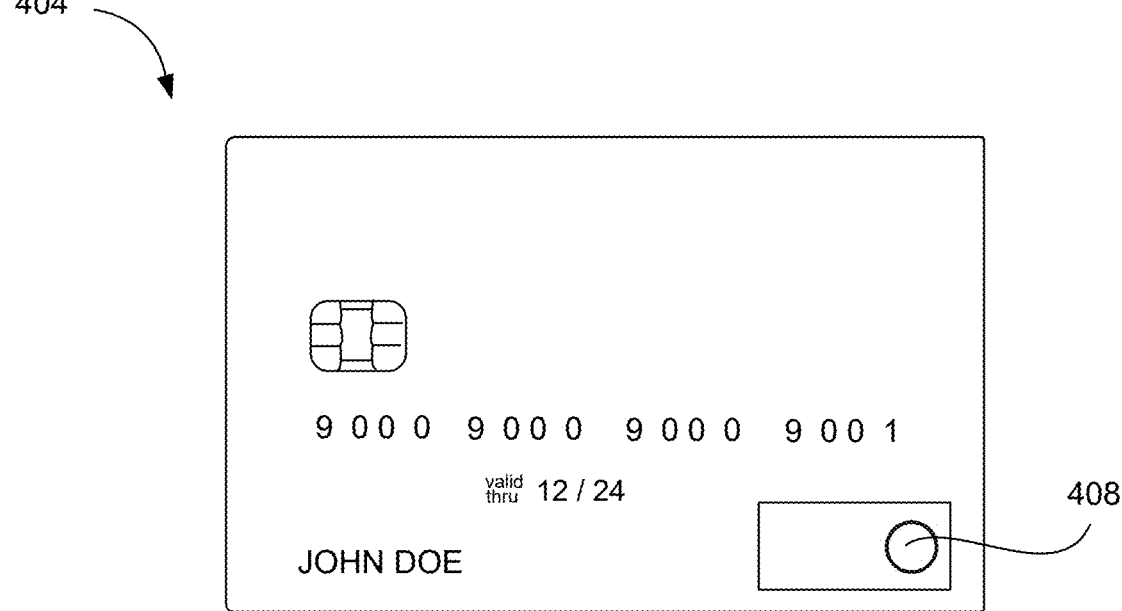
FIG. 9 illustrates a front elevation view of a second membership card of a membership card assembly.
Figure 10:
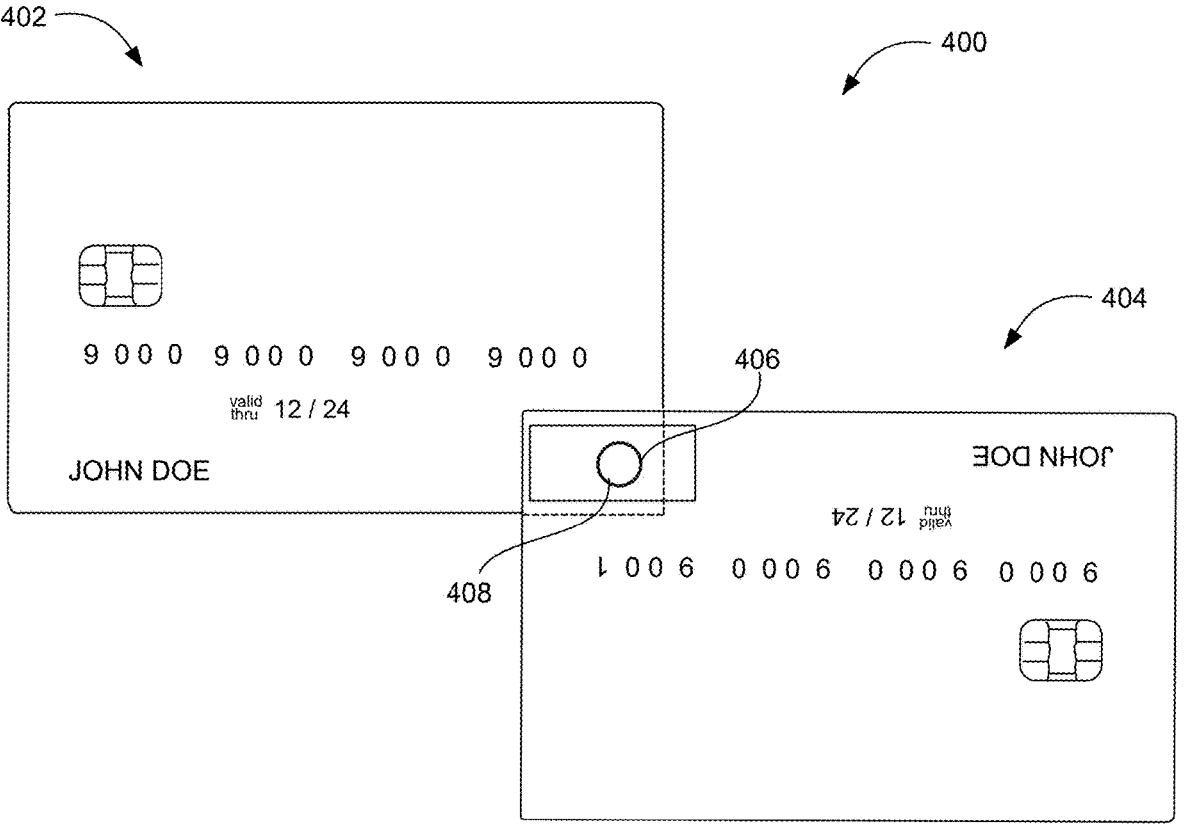
FIG. 10 illustrates a front elevation view of a membership card assembly assembled.

Referring to FIGS. 8-10, in some embodiments, a membership card assembly 400 comprises a first membership card 402 and a second membership card 404, each allowing access to a distinct account, the two cards 402, 404 coupled together. For example, first membership card 402 may comprise a first grommet 406 and second membership card 404 may comprise a second grommet 408. Referring to FIG. 10, the two cards 402, 404 may then be rotatably coupled to one another via the grommets 406, 408. The cards 402, 404 may then rotate away from each other depending on which card needs to be used. It will be appreciated that the membership card assembly 400 allows a user to access all accounts and personal information from both cards carried together. It will further be appreciated that the first and second cards 402, 404 may be attached at a location (e.g., bottom corner) that does not obstruct the function of the card, allowing the respective insertable chips, magnetic strips, or wireless chips to be usable while coupled.

It will be appreciated from the foregoing that the healthcare cards and assemblies disclosed herein solve the need for a healthcare membership card that allows an individual to directly pay money before, during, or after a medical procedure to a healthcare provider from a health savings account and/or a health share, and that also provides easy access to individual/health information. This reduces the time required to pay bills and also allows the patient to be informed as to the cost of the procedure, among other things.

It will also be appreciated that systems and methods according to certain embodiments of the present disclosure may include, incorporate, or otherwise comprise properties or features (e.g., components, members, elements, parts, and/or portions) described in other embodiments. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment unless so stated. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention.

What is claimed is:

1. A healthcare membership card, comprising:
a first surface and an opposite second surface;
a first payment interface disposed on the first surface and encoded to access a first account, the first account corresponding to a health savings account;
a second payment interface disposed on the second surface and encoded to access a second account, the second account corresponding to a health sharing account;
an electromagnetic-shielding layer interposed between the first surface and the second surface, the electromagnetic-shielding layer being configured to attenuate electromagnetic energy such that, when the first surface is presented to a reader, the reader does not read the second payment interface, and when the second surface is presented to the reader, the reader does not read the first payment interface; and
wherein the healthcare membership card is configured to initiate direct payment to a healthcare provider from either the first account or second account without a reimbursement workflow.

2. The healthcare membership card of claim 1, wherein the first account is accessed via a first magnetic stripe and the second account is accessed via a second magnetic stripe.

3. The healthcare membership card of claim 1, wherein the first account is accessed via a first chip and the second account is accessed via a second chip.

4. The healthcare membership card of claim 3, wherein the first and second chips are wireless chips configured for tapping.

5. The healthcare membership card of claim 4, further comprising a faraday slip cover configured to receive at least a portion of the membership card and to enable user selection of which wireless chip is readable by selectively exposing only the corresponding first or second wireless chip to the reader, the remaining portion with the corresponding first or second wireless chip remaining concealed within the faraday slip cover.

6. The healthcare membership card of claim 1, further comprising a machine-readable code configured to access user health information.

7. A healthcare membership card, comprising:
a first portion comprising a first wireless chip, the first wireless chip configured to access a health savings account;
a second portion comprising a second wireless chip, the second wireless chip configured to access a health sharing account; and
a faraday slip cover configured to prevent a chip reader from reading the first and second wireless chips simultaneously and to enable user selection of which wireless chip is readable by selectively exposing only the corresponding portion to the reader, the remaining portion remaining concealed within the faraday slip cover.

8. A method of using a healthcare membership card for paying a healthcare provider, comprising:
using a faraday slip cover to selectively expose a first portion of the healthcare membership card, the first portion encoded to access a health savings account;
concealing a second portion of the healthcare membership card within the faraday slip cover, the second portion encoded to a health sharing account;
tapping the exposed first portion to make a payment from the health savings account; and
scanning a machine-readable code on the healthcare membership card to access a patient health record after passcode authentication.

* * * * *